US00PP27251P3

(12) United States Plant Patent
Lee

(10) Patent No.: US PP27,251 P3
(45) Date of Patent: Oct. 11, 2016

(54) ***LOROPETALUM* PLANT NAMED 'SHANG-GREEN'**

(50) Latin Name: *Loropetalum chinensis*
Varietal Denomination: SHANG-GREEN

(71) Applicant: Robert Edward Lee, Independence, LA (US)

(72) Inventor: Robert Edward Lee, Independence, LA (US)

( * ) Notice: Subject to any disclaimer, the term of this patent is extended or adjusted under 35 U.S.C. 154(b) by 150 days.

(21) Appl. No.: 14/121,179

(22) Filed: Aug. 11, 2014

(65) Prior Publication Data

US 2016/0044846 P1 Feb. 11, 2016

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Loropetalum* cultivar named 'SHANG-GREEN' is disclosed, characterized by distinctive upright, dense plant growth. Foliage is small and green. The new cultivar is a *Loropetalum*, suitable for ornamental garden purposes.

2 Drawing Sheets

Figure 1:
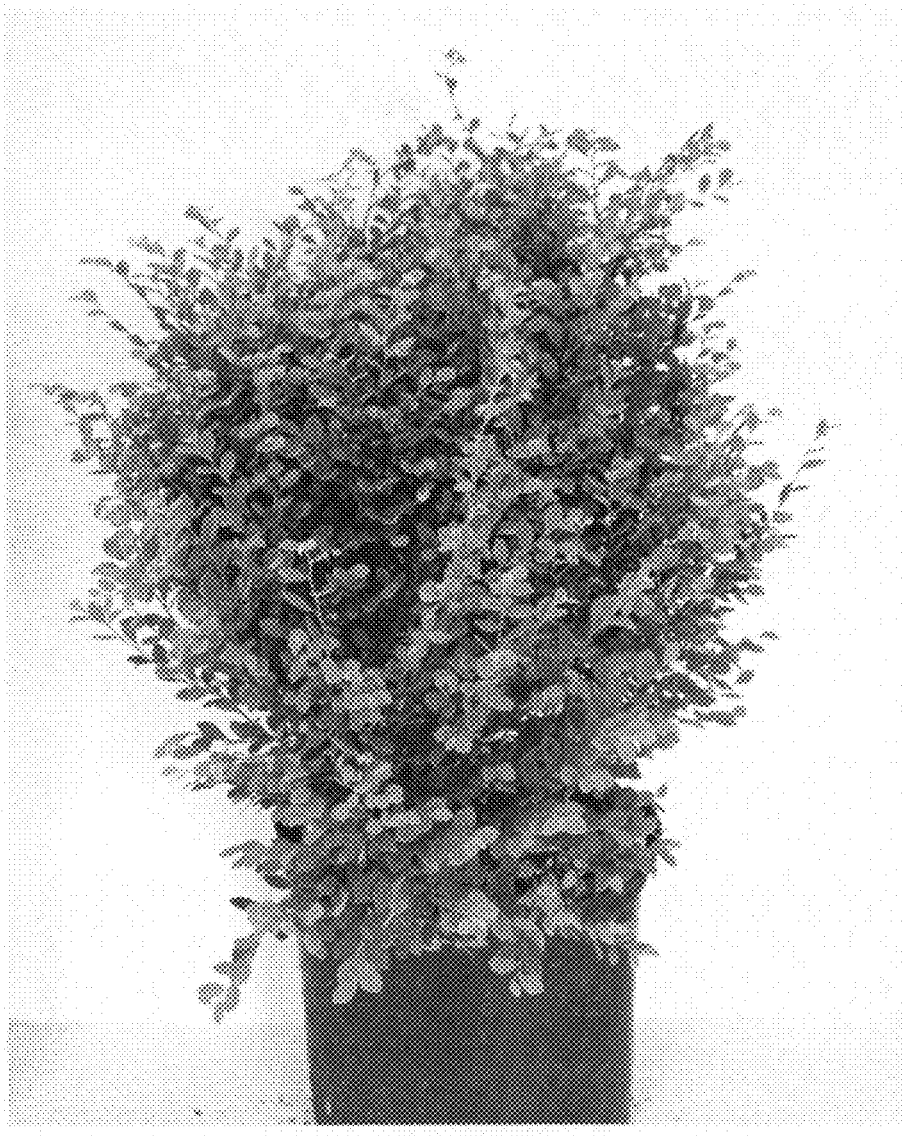

Latin name of the genus and species: *Loropetalum chinensis*.

Variety denomination: 'SHANG-GREEN'.

BACKGROUND OF THE INVENTION

The new cultivar is a product of a planned breeding program by the inventor. This new variety was found as an openly pollinated seedling in a group of unnamed, unpatented *Loropetalum chinensis* by the inventor, Robert Edward Lee, in Independence, La., at a research nursery.

After identifying the new variety as a potentially interesting selection, the inventor first organized propagation of 'SHANG-GREEN' by vegetative cuttings during 2004 at the same commercial nursery in Independence, La. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'SHANG-GREEN' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SHANG-GREEN' These characteristics in combination distinguish 'SHANG-GREEN' as a new and distinct *Loropetalum* cultivar:

1. Controlled growth habit
2. Small green foliage
3. Dense plant growth
4. Upright plant habit
7. Good landscape performance
8. Good container plant
9. Hardy to USDA Zone 7

COMPARISON TO PARENT VARIETY

'SHANG-GREEN' is similar in most horticultural characteristics to the assumed seed variety, an unnamed plant of *Loropetalum chinensis*. Plants of the new cultivar 'SHANG-GREEN' however, are more upright in plant habit, with dense branches and small foliage.

Pollen parent is unknown.

COMMERCIAL COMPARISON

'SHANG-GREEN' can be compared to the commercial variety *Loropetalum chinensis* 'SHANG-WHITE', U.S. Plant Pat. No. 21,738. Plants of the new cultivar 'SHANG-GREEN' are similar to plants of 'SHANG-WHITE' in most horticultural characteristics, however, plants of the new cultivar 'SHANG-GREEN' are more upright, denser with smaller foliage.

BRIEF DESCRIPTION OF THE PHOTOGRAPHS

The accompanying photograph in FIG. 1 illustrates in full color a plant of 'SHANG-GREEN' grown outdoors in Alabama.

Figure 2:
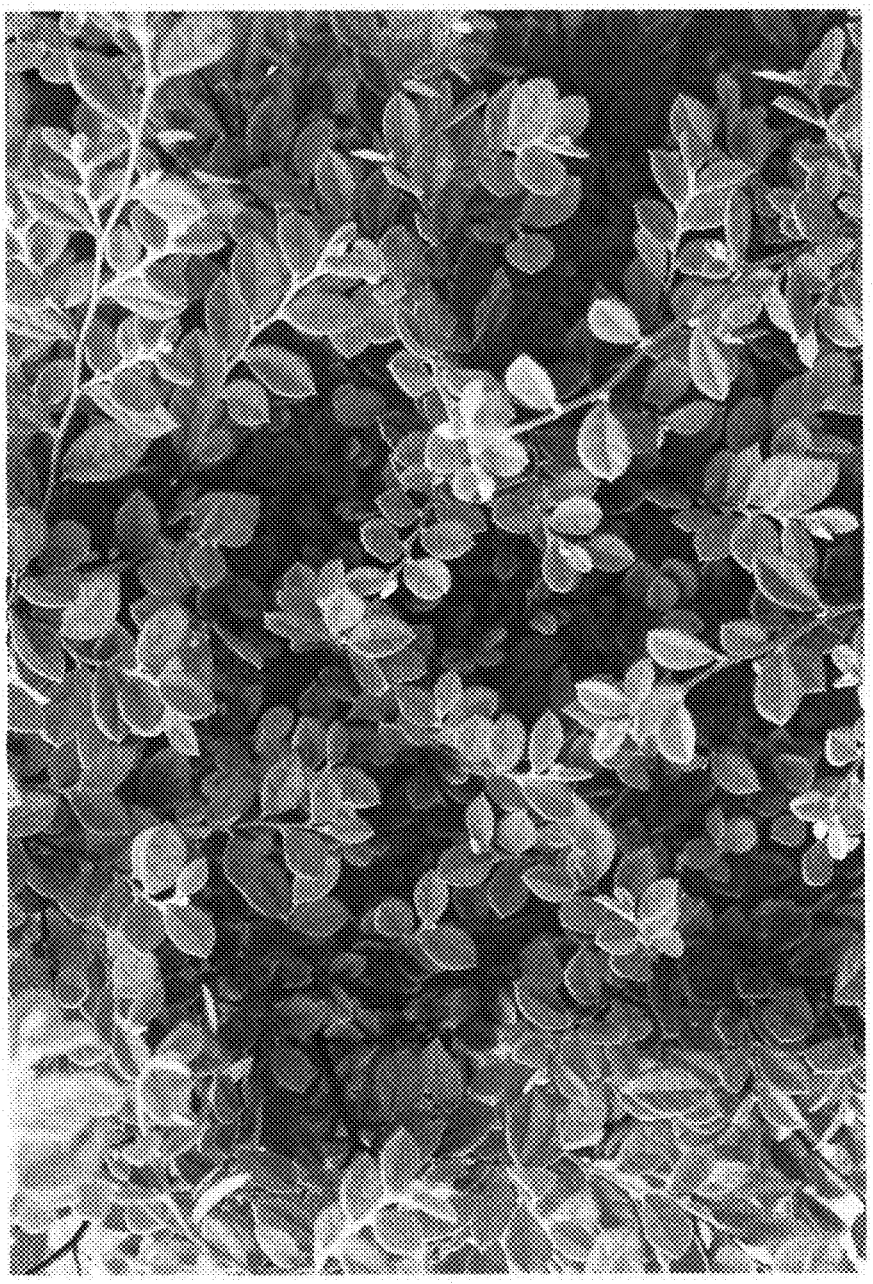

FIG. 2 shows a close up of typical foliage of the new variety. The plant is approximately 3 years old, and is shown in a three gallon container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SHANG-GREEN' plants grown outdoors in Loxley, Ala. Plants are approximately 3 years old, in a 3 gallon nursery container. Measurements and numerical values represent averages of typical plant types.

Botanical classification: *Loropetalum chinensis* 'SHANG-GREEN'.

PROPAGATION

Typically by semi-hardwood cuttings in spring and summer.

*Root description*.—Mainly fibrous, larger roots semi-wood. Colored near RHS Grey-Brown 199D.

PLANT

Growth habit: Globular shrub.

Height: Approximately 60 cm to top of foliar and flowering plane.

Plant spread: Approximately 50 cm.

Branching characteristics: Average 4 primary lateral branches emerge from a pinch. Branches occur at approximately 45° angles. Small, secondary lateral branches are densely arranged, approximately 1.5 cm apart.

Primary branches:

*Length of primary branches*.—Average 25 cm, then pinched and new branches emerge.

*Diameter of primary branches*.—Approximately 1.0 cm.

*Primary branch strength*.—Very strong, difficult to break.

*Primary branch color*.—Mature branches near RHS Grey-Brown N199A. Young branches near Brown 200C.

*Primary branch texture*.—Mature branches rough but not scaly. Young growth rough and slightly scaly.

Age of plant described: Approximately 3 years.

Internode length: Average range of 1.5 to 4.5 cm.

FOLIAGE

Leaf:

*Type*.—Simple.

*Arrangement*.—Alternate.

*Average length*.—Approximately 1.9 cm.

*Average width*.—Approximately 0.9 cm.

*Shape of blade*.—Ovate.

*Apex*.—Acute or abruptly acuminate.

*Base*.—Rounded.

*Attachment*.—Stalked.

*Margin*.—Entire.

*Texture of top surface*.—Pubescent

*Texture of bottom surface*.—Pubescent.

*Appearance of top surface*.—Matte.

*Appearance of bottom surface*.—Matte.

*Color*.—Young foliage upper side: Near RHS Green 138A. Young foliage under side: Near RHS Green 138B. Mature foliage upper side: Near RHS Green 137C. Mature foliage under side: Near RHS Green 138B.

Venation:

*Type*.—Pinnate.

*Venation color upper side*.—Near RHS Green 137B.

*Venation color under side*.—Near RHS Green 137C.

Petiole:

*Length*.—About 0.25 cm.

*Diameter*.—About 0.1 cm.

*Color*.—Upper Surface: Near RHS Yellow-Green 152B. Lower Surface: Near RHS Yellow-Green 152D.

FLOWER

Natural flowering season: Flowering typically begins around March, in California or Alabama, flowering heavily until April. Re-blooming occurs throughout Spring and Summer.

Inflorescence and flower type and habit: Raceme of, perfect flowers, asymmetrical flowers. 2 to 6 typically occur at a terminal leaf axil, facing outwardly.

Flowers per plant: Approximately 200 flowers on a mature plant of 2 to 3 years.

Flower longevity on plant: Approximately 1 week for individual flowers.

Persistent or self-cleaning: Self-cleaning.

Inflorescence:

*Flowers per raceme*.—Typically 2 to 6.

*Diameter*.—Average 6.0 cm.

*Height*.—Average 4.9 cm.

Flower size (petals and sepals only, not including protruding stamen and style):

*Diameter*.—Average 2.0 cm.

*Length*.—Average 1.5 cm.

Bud:

*Shape*.—Oblong.

*Length*.—0.5 cm.

*Diameter*.—0.2 cm.

*Color*.—Near RHS Green-White 157B.

Corolla:

*Petals*.—Number: Average 4. Arrangement: Asymmetrical single whorl. Petals occurring to one side. Length: Approximately 1.0 cm. Width: Approximately 0.2 cm. Shape: Lanceolate. Aspect: Undulating. Margin: Entire. Texture: Glabrous, all surfaces. Appearance: Matte. Apex: Obtuse, rounded.

*Color*.—When opening: Upper surface: Near RHS White 155C, flushed Green-White 157D near base. Lower surface: Near RHS White 155C, flushed Green-White 157D near base. Fully opened: Upper surface: Near RHS White 155D. Lower surface: Near RHS White 155D. Fading: Upper surface: Near RHS White 155D. Lower surface: Near RHS White 155D.

Calyx:

*Sepals*.—Arrangement: Single asymmetrical whorl. Quantity: 4. Length: Average 3 mm. Width: Average 2 mm. Shape: Deltoid. Sepal texture: Glabrous all surfaces. Appearance: Matte. Apex: Acute. Color: Upper Surface: Near RHS Green 138B. Lower Surface: Near RHS Green 138A.

*Fragrance*.—None.

Peduncle:

*Length*.—Average 0.8 cm.

*Diameter*.—0.1 cm.

*Texture*.—Pubescent.

*Color*.—Near RHS Green 138A.

*Orientation*.—Approximately 15 to 45 degrees angle of emergence, straight to occasionally curved.

*Strength*.—Strong and flexible.

REPRODUCTIVE ORGANS

Androecium:

*Stamens*.—Number (per flower): Typically 8. Filament length: Average 1 mm. Filament color: Near RHS White 155C.

*Anthers*.—Shape: Linear. Length: Less than 1 mm. Color: Near RHS White 155C.

*Pollen*.—Amount: Scant. Color: Near RHS White 155B.

Gynoecium:

*Pistils*.—Quantity per flower: 1. Length: Approximately 1 mm.

*Style*.—Length: Less than 1 mm. Color: Near RHS White 155D.

*Stigma*.—Shape: Linear. Color: Near RHS White 155D. Ovary: Less than 1 mm, colored near Yellow-Green 150D.

OTHER CHARACTERISTICS

Disease and pest resistance: Not observed to be susceptible nor resistant to normal diseases and pests of *Loropetalum*.

Temperature tolerance: USDA Zone 7 through 10.

Fruit/seed production: Seeds not common. If produced, 1 or 2 per flower. Approximately 5 mm long and 2 mm wide. Colored near Green 138B.

What is claimed is:

1. A new and distinct cultivar of *Loropetalum* plant named 'SHANG-GREEN' as herein illustrated and described.

* * * * *